United States Patent
Heng

Patent Number: 5,252,075
Date of Patent: Oct. 12, 1993

[54] MEDICAL PERSONNEL AND PATIENT COMMUNICATION INDICATOR DEVICE

[76] Inventor: Di Heng, 39 Bowery #609, New York, N.Y. 10002

[21] Appl. No.: 860,133

[22] Filed: Mar. 30, 1992

[51] Int. Cl.$^5$ .......................... G09B 21/00; G09B 7/00
[52] U.S. Cl. ..................................... 434/112; 434/342
[58] Field of Search ............... 434/112, 327, 342, 370

[56] References Cited

U.S. PATENT DOCUMENTS

| | | | |
|---|---|---|---|
| 3,228,118 | 1/1966 | Hirtle | 434/342 |
| 3,651,512 | 3/1972 | Summers | 340/286 |
| 3,685,169 | 8/1972 | Blau et al. | 434/342 |
| 3,735,500 | 5/1973 | Matsumoto | 434/342 |
| 3,925,779 | 12/1975 | Gerstenhaber | 340/337 |
| 4,165,890 | 8/1979 | Leff | 283/7 |
| 4,306,368 | 12/1981 | Coghill et al. | 40/496 |
| 4,761,633 | 8/1988 | Leff et al. | 340/286 R |
| 4,915,632 | 4/1990 | Leff et al. | 434/112 |

Primary Examiner—Gene Mancene
Assistant Examiner—Cindy A. Cherichetti

[57] ABSTRACT

An easy to operate communication device consisting of a lighted information screen which is made up of subunits of data segments that can be further selectively highlighted. This device actually consists of twin units of the above, one unit contains the questions and requests to be highlighted, while the second unit contains the responses and instructions.

1 Claim, 6 Drawing Sheets

FIG. 4 A

| Light | | Connection to central nursing station | |
|---|---|---|---|
| Patient's abnormal sensation, reaction or calling for help | | Occuring on which parts of body | |
| Written language | Pictoral language | Written language | Pictoral language |
| Acute emergency situation including heart attack short of breath, wheezing, coma | Picture of patient lying on the floor struggling & calling for help | The whole body | Picture of the whole body |
| Aches and pains, soreness or tension & similar uncomfortable sensation | Picture of facial expression of suffering | Head & Face | Front view of head & face |
| Reaction to oral medicine or injection and discomfort of different degree | Picture of a pill in stomach & picture of person in discomfort | Neck & Chest | Front view of neck & chest |
| Chilles, tremor, heat intolerance, profuse sweating etc abnormal reaction | Picture of person having chill, picture of person sweating | Back of neck & back of chest | Back view of neck & chest |

FIG. 4 B

| | | | |
|---|---|---|---|
| Pins & Needles sensation numbness due to poor circulation, feeling that one has to move a part of body in order to become more comfortable | Picture of body part being compressed & picture of blocked circulation | Abdomen, external genitals | Front view of abdomen & genitals |
| Want to urinate or pass stool or having wet the bed, soiled the bed | Picture of toilet bowl | Waist and Buttock | Back view of lower torso, including waist |
| Wheezing or coughing, vomiting, needs to spit | Picture of patient vomiting, coughing, spitting | Upper limbs | Picture of arms and hands |
| Extremely hungry or thirsty, want to eat or drink | A cup of water, a plate of food | Lower limbs | Both thighs, legs and feet |
| Afraid of light, afraid of loud noise, restless, fearful of surrounding | Picture of tearful expression; expression of confrontation with bright light & loud noise shaking up the ear | Left half of body | Whole view of left half of body |
| Need help with contacting relatives and answering letters | Picture of nursing staff standing by patient | Right half of body | Whole view of right half of body |

FIG. 5 A

| Light | | Connection to central nursing station | |
|---|---|---|---|
| Instruction to patients or answers to patient's requests and queries | | How much later action will be taken if it cannot be done at once | |
| Written language | Pictoral language | Written language | Pictoral language |
| Doctor will be here to check you for diagnosis and treatment | Picture of doctor listening to patient with stethoscope | Please wait 5 minutes | Two clock faces showing 3 p.m. and 3:05 p.m. |
| Nurse will be here to relieve your pain, clean your urine and stool and make you comfortable | Picture of nurse massaging patient | Please wait 15 minutes | Two clock faces 9:15 and 9:30 |
| Please cooperate with medical personnel, for the best results in diagnosis and treatment | Patient extend to arm to receive injection from nurse | Please wait 1 hour | Two clock faces 4 and 5 o'clock |
| This is a temporary reaction, it will be over very quickly we will give you additional diagnosis and treatment as appropriate | Picture of painful face at 3:10 changing to happy face at 3:30 | Please wait till afternoon | Two 24 - hour clock face 10 a.m. in one 3 p.m. on the other |
| Temporarily you are not allowed to eat or drink; please be patient | Picture of a cup, and a plate of food with stop sign | Please wait till tomorrow | Picture of thumbing through one leaf in a day - to - day calender |

FIG. 5 B

| You are not allowed to move your body temporarily; we cannot help you to bathroom at present | Picture of patient lying down with thigh pulled and a stop sign on the thigh signifying that movement is forbidden | Please wait several days | Thumbing through several leaves of a day - to - day calender |
|---|---|---|---|
| Please calm down, someone will be here to remove your discomfort and take care of unsatisfactory situations | Nurses checking on surrounding medical equipment etc | Please wait Patiently, there won't be a mistake | A clock face without hands and a happy face |
| We already know your request, however, what you want can undo the benefits of your treatment. Therefore, we cannot honor your request | Picture of a bottle liquor & a glass of liquor with the sign of stop on both | Unsatisfactory situations are over. All are completed | Picture of spring time sunlight melting snow from winter |
| Please don't be nervous. Your illness will get better. Please rest well or sleep well | Picture of patient feeling at ease and thinking of the future with robust health | Yes, we agree | ✓ |
| Your relatives and friends will be here to visit you. What you asked us to do, we will do it. | Picture of friends and relatives by patient bedside | No, we don't agree | X |

MEDICAL PERSONNEL AND PATIENT COMMUNICATION INDICATOR DEVICE

BACKGROUND OF THE INVENTION

Close cooperation and good coordination between medical personnel and patients is a basic factor contributing to optimal diagnosis and treatment. To achieve this end, the most important condition is that medical personnel including doctors, nurses, administrators) and patients (including accompanying friends and relatives) must be able to have timely communications. Patients should be able to timely and accurately express one's own sensations, experience and reactions. Such information is the most important link to diagnosis and treatment. Similarly, medical personnel by rules and regulation should be able to give proper directions, and explanations to patients and their relatives and solve patient's problems and needs.

However, as a result of language barriers or extreme physical weakness resulting in inability to make adequate volume in speaking or to articulate clearly, communication difficulty often arises in hospitals, nursing homes and rehabilitation centers. Delays and misunderstandings in communication reduces therapeutic effectiveness, delays in therapy, unnecessary incidents, and in the case of medical emergencies, the detrimental effects are even more obvious.

In order to reduce such regretful incidents, the inventor has designed a convenient, easy to operate and effective "communication display indicator."

SUMMARY OF THE INVENTION

Concise data for informational exchange between medical personnel and patients is displayed on L C D screen or video screen, plus numerous other methods. The current model employs the simplest, inexpensive, easily controllable electrically lighted display.

This invention consists of 3 parts

1. A unit that displays information patients want to express This unit is called INFORMATION - UNIT A.
2. A unit that displays information medical personnel want to express. This unit is called INFORMATION - UNIT B.
3. Accessories connecting A and B.

BRIEF DESCRIPTION OF THE DRAWINGS

Complete Description of the Invention is Consisted in 5 Drawings

FIG. 3 INFORMATION - UNIT A in combination with INFORMATION - UNIT B

FIG. 4 Information content of INFORMATION - UNIT A information that patients want to express FIG. 5 Information content of INFORMATION - UNIT B information that medical personnel want to express

DETAILED DESCRIPTION OF THE DRAWINGS

Fig. 1

Figure 1:
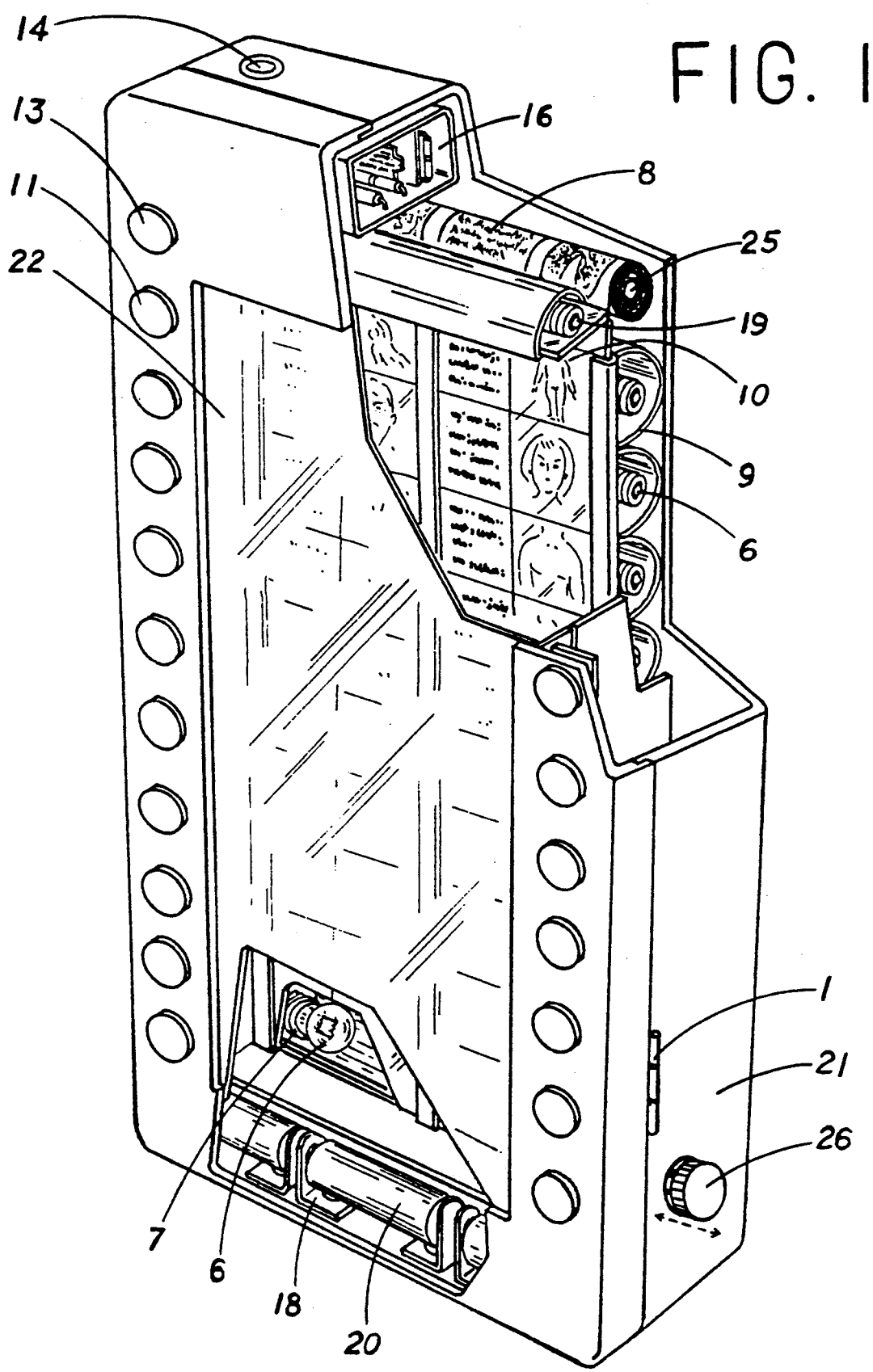
FIG. 1 3 - Dimensional exploded view of the whole invention

3 - Dimensional Exploded View of the Whole Invention

Both INFORMATION - UNIT A and INFORMATION - UNIT B consists of a rectangular box, dimensions as specified in diagram. On the right edge is a hinge 1 enabling the box to be opened for change of spare parts inside the box e.g. informational screen 8, burned - out light bulb, and spent dry - cells 20 etc, and when the box is closed, the clasp 2 on the top - side of INFORMATION - UNIT A and the underside of INFORMATION - UNIT B each has sleeve - type jaws combining to form hinge and coupling 3 and 4 connecting INFORMATION - UNIT A and B together. Locking clamp screw 5 controls the angle that a INFORMATION - UNIT A and B to open like a book.

INFORMATION - UNIT A and B are enclosed in light, comfortable and beautiful casing 21, On the right and left side of the top of INFORMATION - UNIT A and B, are a row of touch buttons, which are actually on off switches 11 activated by light touch only, specially designed with consideration for the impaired physical, mental and visual power of patients.

On the top surface is a magnifying and protective transparent pane 22 Inside the pane is a rectangular information screen 8. On the information screen 8 are several transparent information cards 10, detailed in DIAGRAM 3 and DIAGRAM 4.

To access or change the information contained in the device, the user must rotate the two ends of the information screen 8, which houses a pair of rollers 25, similar to the pair of film rollers in a camera the informations screens data can be rolled back and forth by a winder 26 at the end of the rollers. The film can be removed and change like a roll of camera film, allowing unlimited amount of data for display by this device.

To use this invention in DIAGRAM 1, first light up the complete information screen, then, select the individual data card reflecting the person's idea. Also, one can make different cards to serve different purposes, e. g. A card for child education; a card for the mentally retarded population; testing service; learning toy etc, are all within the scope of this invention.

Each touch button 11 controls a separate tiny light bulb 6 in a socket 7 under the informational screen 8. Each tiny light bulb has a reflector 9, and when turned on by the appropriate touch button 11, can separately light up an information card 10. In addition, there is a central light 19 controlled by switch 12 that can light up the entire information screen 8. However, individual information card 10 can be further more brightly lit by touch - button 11.

On the top right hand corner of both INFORMATION UNIT A and B, there is a socket 14 for wired connection to the central nursing station 24 Switch 13 activates socket 15 and signals the central nursing station 24 There is also remote control emitter 16 and receiver 17 for the same purpose.

In the bottom of INFORMATION - UNIT A and B are compartments for battery packs 20 and conducting clamps 18.

Figure 2:
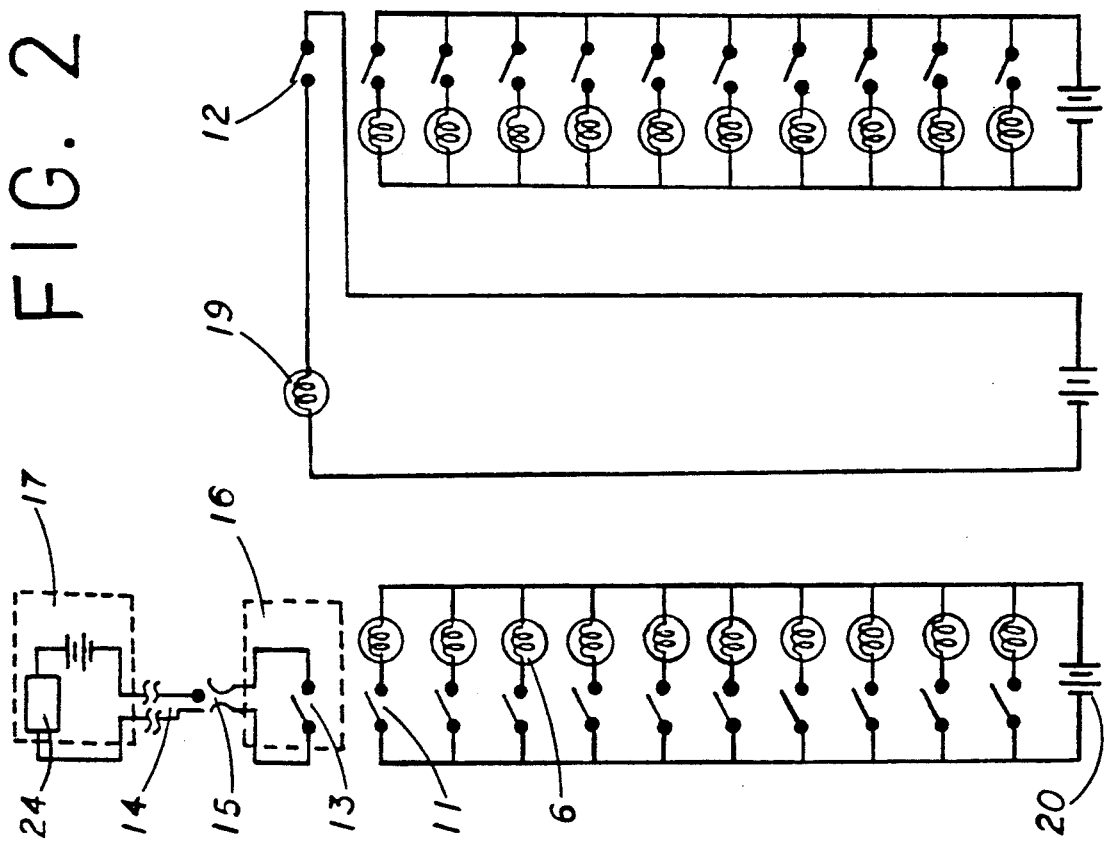
FIG. 2 Circuit diagram of the whole invention

FIG. 2 Circuit Diagram

Circuit diagrams of INFORMATION - UNIT A and B are identical.

Switch 11 controls a tiny light bulb arranged in parallel on power source 20

In addition, there is a connector to the central nursing station 24, either wired 14, 15 or wireless 16, 17.

Telephone or intercom can also be connected to this device.

Figure 3:
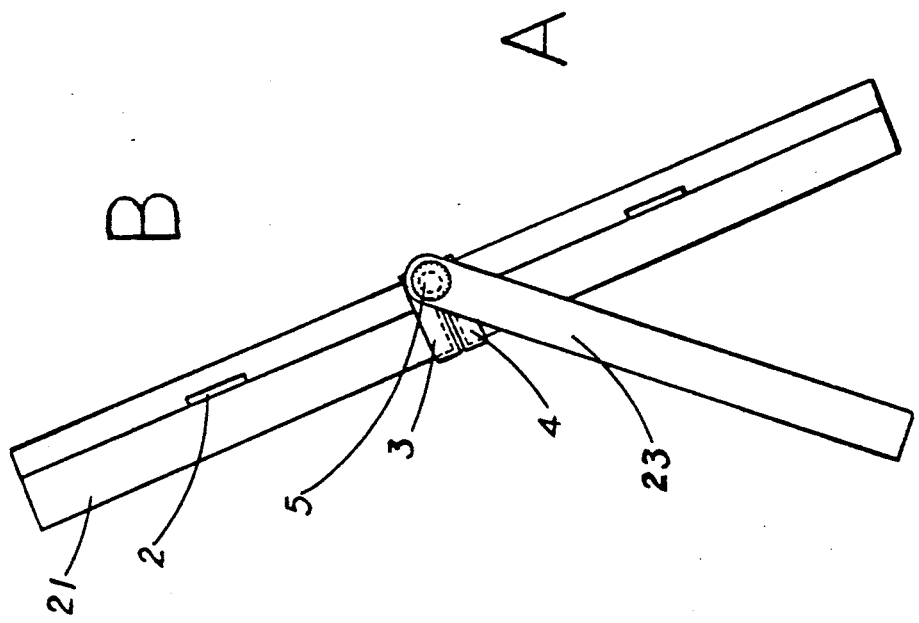

FIG. 3 Diagram 3 demonstrates INFORMATION - UNIT A unit in combination with INFORMATION -

UNIT B, and A separating from B . An accessory sleeve - type jaw 3 and 4 combines A and B together, and also enables A and B to be separated. The angle of frame support 23 can the adjusted using locking clamping screw 5 so that INFORMATION - unit A and B can be angled properly to accommodate different individual circumstances.

OPERATING INSTRUCTIONS

To use this medical personnel patient communication device, INFORMATION - UNIT A and B are normally closed, so, open it up. Then, adjust 5 so that A and B are now adjusted to proper position. Adjust support frame 23 to proper angle to separate A and B, for separate usage.

Press button 12 to turn on lighting 19. The whole information screen 8 is now lit. The user can see all of the information contents clearly. Then, select the particular item one wants to express. By pressing one or more buttons 11 adjacent to data segments 10 The tiny light bulbs 6 controlled by these buttons now light up and the corresponding data segments are now brightly lit If a patient wants to talk about his headache, he presses button 11 next to the headache data segment and that segment brightly lights. The medical personnel knows at once the patient has headaches. Pressing button 11 once more will turn it off.

I claim:

1. A device for displaying information for communication with handicapped, infirm, illiterate, or non-english speaking persons comprising:
    a casing,
    a plurality of removable and interchangeable information screens made of transparent material and having a plurality of information cards thereon for insertion in the casing,
    said information cards having imprinted thereon information that patients want to express, or information that service providers want to get across to patients,
    rollers attached to each end of said information screen for advancing the screen and for providing easy insertion and removal of the screen from the casing,
    and highlighting means in said casing for highlighting an individual information card by illumination of the card.

* * * * *